United States Patent [19]

Maurer et al.

[11] Patent Number: 4,774,233
[45] Date of Patent: Sep. 27, 1988

[54] PESTICIDALLY ACTIVE O-ETHYL O-ISOPROPYL O-(2-TRIFLUOROMETHYLPYRIMIDIN-5-YL)-PHOSPHORIC ACID ESTER

[75] Inventors: Fritz Maurer, Wuppertal; Bernd Baasner; Bernhard Homeyer, Leverkusen; Wolfgang Behrenz, Overath; Wilhelm Stendel, Wuppertal, all of Fed. Rep. of Germany

[73] Assignee: Bayer Aktiengesellschaft, Leverkusen, Fed. Rep. of Germany

[21] Appl. No.: 891,002

[22] Filed: Jul. 25, 1986

[30] Foreign Application Priority Data

Aug. 7, 1985 [DE] Fed. Rep. of Germany ....... 3528264

[51] Int. Cl.⁴ .......................... C07F 9/65; A61N 57/16
[52] U.S. Cl. ........................................ 514/86; 544/243
[58] Field of Search ........................... 544/243; 514/86

[56] References Cited

U.S. PATENT DOCUMENTS 4,486,422 12/1984 Costales et al. ..................... 514/86
4,558,039 12/1985 Reifschneider et al. ............. 514/86
4,666,894 5/1987 Maurer et al. ........................ 514/86

FOREIGN PATENT DOCUMENTS 3317824 11/1984 Fed. Rep. of Germany .
2230651 12/1974 France .

Primary Examiner—Donald G. Daus
Assistant Examiner—Diane A. Rivers
Attorney, Agent, or Firm—Sprung Horn Kramer & Woods

[57] ABSTRACT

O-Ethyl O-isopropyl O-(2-trifluoromethyl-pyrimidin-5-yl)-phosphoric acid ester of the formula

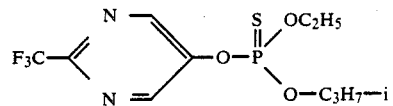

is insecticidally and nematocidally active.

3 Claims, No Drawings

PESTICIDALLY ACTIVE O-ETHYL O-ISOPROPYL O-(2-TRIFLUOROMETHYLPYRIMIDIN-5-YL)-PHOSPHORIC ACID ESTER

The invention relates to a new 2-trifluoromethyl-pyrimidin-5-yl-phosphoric acid ester, a process for its preparation and its use as an agent for combating pests, in particular as an insecticide and a nematicide.

It is known that certain O-pyrimidinylphosphoric (phosphonic) acid esters and ester-amides, such as, for example, O,O-diethyl-O-O(2-tert.-butyl-pyrimidin-5-yl)thionophosphoric acid ester, O-ethyl-O-(2-i-propyl-pyrimidin-5-yl)-N-i-propyl-thionophosphoric acid ester-amide and O-ethyl-O-i-propyl-O-(2-tert.-butyl-pyrimidin-5-yl) acid ester, have an insecticidal action (compare DE-OS (German Published Specification) No. 2,643,262, DE-OS (German Published Specification) No. 3,317,824 and U.S. Pat. No. 4,429,125).

However, the action of these compounds is not always completely satisfactory under certain circumstances, especially with low concentrations of active compound and when low amounts are applied.

The new compound of the formula (I) shows an excellent insecticidal and nematocidal activity. It is particularly valuable for the long term control of soil insects as *Diabrotica balteata* and *Phorbia antiqua,* aphids, as *Myzus persicae* and nematodes, as *Meloidogyne incognita.* A long term activity is for the control of soil insects of a particular importance. The active ingredient can be applied to the soil, to plant parts which are in or near the soil or to the seeds.

The new O-ethyl-O-i-propyl-O-(2-trifluoromethyl-pyrimidinyl-5-yl)-thionophosphoric acid ester of the formula (I)

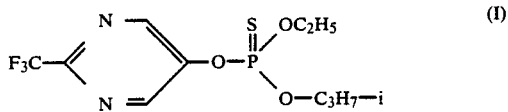

had now been found.

The new O-(2-trifluoromethyl-pyrimidin-5yl)-phosphoric acid ester of the formula (I) is obtained by a process in which 5-hydroxy-2-trifluoromethyl-pyrimidine of the formula (II)

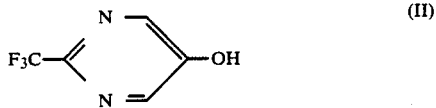

or the corresponding alkali metal, alkaline earth metal or ammonium salts, is/are reacted with the halide of the formula (III)

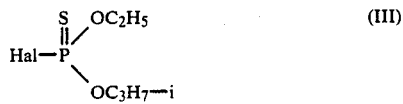

in which Hal represents halogen (preferably chlorine or bromine), if appropriate in the presence of an acid acceptor and if appropriate in the presence of a diluent.

The new O-(2-trifluoromethyl-pyrimidin-5-yl)phosphoric(phosphonic) acid ester of the formula (I) is distinguished by a high activity as an agent for combating pests, in particular by its outstanding insecticidal and nematicidal action.

If 5-hydroxy-2-trifluoromethylpyrimidine and O-ethyl-O-i-propyl-thionophosphonic acid diester-chloride are used as starting substances for the process according to the invention, the corresponding reaction can be outlined by the following equation:

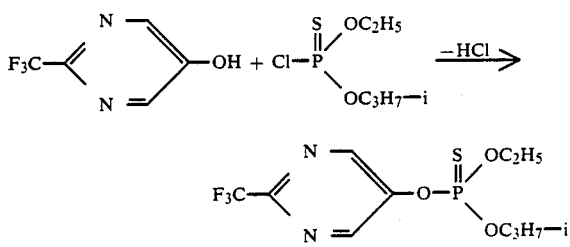

Formula (II) provides a definition of the 5-hydroxy-2-trifluoromethyl-pyrimidine and salts thereof to be used for the process according to the invention. Sodium, potassium, calcium and ammonium salts are preferably used as the alkali metal, alkaline earth metal or ammonium salts.

Examples which may be mentioned of the starting substances of the formula (II) are: the sodium, potassium, calcium and ammonium salt of 5-hydroxy-2-trifluoromethyl-pyrimidine.

The compound of the formula (II) can be prepared by a process in which 5-fluoro-2-trifluoromethyl-pyrimidine of the formula (IV)

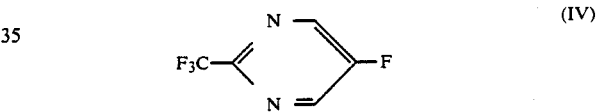

is reacted in the presence of aqueous acid acceptors, such as, for example, sodium hydroxide, and in the presence of inert diluents, such as, for example, ethylene glycol dimethyl ether, at temperatures between 50° C. and 180° C. and the mixture is then acidified by addition of mineral acids, such as, for example, hydrochloric acid [compare Example (II-1)], and the compound of the formula (II) is isolated by customary methods.

The compound of the formula (IV) is known (compare, for example, DE-OS (German Published Specification) No. 3,402,194).

The compounds of the formula (III) are known and/or can be prepared by generally known processes and methods (compare, for example, Methoden der organischen Chemie (Methods of Organic Chemistry) (Houben-Weyl-Müller), 4th edition, Volume 12/1 (1963), pages 415–420 and pages 560–563; Volume 12/2 (1964), pages 274–292, pages 405–408 and pages 607–618, pages 621–622 and pages 755–757; Thieme-Verlag Stuttgart).

The process according to the invention for the preparation of the new compound of the formula (I) is preferably carried out using diluents. Possible diluents are virtually all the inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethylsulphoxide, tetramethylene sulphone and hexamethylphosphoric acid triamide.

If appropriate, the process can be carried out in the presence of acid acceptors. Possible acid acceptors are all the customary acid-binding agents. Alkali metal carbonates and alcoholates, such as sodium carbonate and potassium carbonate and sodium methylate or ethylate and potassium methylate or ethylate, and furthermore aliphatic, aromatic or heterocyclic amines, for example triethylamine, trimethylamine, dimethylaniline, dimethylbenzylamine and pyridine, have proved particularly useful.

The process according to the invention is in general carried out at temperatures between 0° C. and 120° C. The range between 10° C. and 100° C. is preferred. The reactions are in general carried out under normal pressure.

The starting substances (II) and (III) are usually employed in approximately equimolar amounts for carrying out the process according to the invention. An excess of one or the other of the reaction components provides no substantial advantages.

The reactions are in general carried out in a suitable diluent and if appropriate in the presence of an acid acceptor. Working up is effected by customary methods. The new compound is obtained in the form of an oil, which cannot be distilled without decomposition but can be freed from the last volatile constituents by so-called "incipient distillation", that is to say prolonged heating to a moderately elevated temperature under reduced pressure, and purified in this manner. It is characterized by its refractive index.

The active compound is well tolerated by plants, has a favorable level of toxicity to warm-blooded animals, and is suitable for combating animal pests, especially insects, arachnida and nematodes, which are encountered in agriculture, in forestry, in the protection of stored products and of materials, and in the hygiene field. It is active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera Spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanic, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticuliermes spp. From the order of the Anoplura, for example *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicornye brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia lituria,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus Gibbium psylloidses,* Tribolium spp., Tenebrio molitor, Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.* From the order of the Acarina, for example, *Acarus siro,* Argas spp., Ornithodoros spp., *Dermanyssus gallinae, Eriophyses ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus*

*semipenetrans*, Heterodera spp., Meloidogyne spp., Aphelenchoides spp., Longidorus spp., Xiphinema spp. and Trichodorus spp.

The active compound of the formula (I) is distinguished by an outstanding insecticidal and nematicidal activity. When used as soil insecticides in particular, it displays an outstanding action against grubs, such as, for example, Phorbia antiqua grubs, and leaf aphids, such as, for example, Myzus persicae. It also exhibits a very good activity when used against nematodes, such as, for sample, Meloidogyne incognita.

The compound is thus particularly suitable for use for combating soil insects and nematodes.

The compound according to the invention can furthermore be employed for combating hygiene pests and pests of stored products.

The new compound furthermore shows an action as a leaf insecticide and an acaricide.

The active compound can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compound with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compound according to the invention can furthermore be present in its commercially available formulations and in the use forms, prepared from these formulations, as a mixture with synergistic agents. Synergistic agents are compounds which increase the action of the active compound, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compound is employed in a customary manner appropriate for the use forms.

When used against hygiene pests and pests of stored products, the active compound is distinguished by an excellent residual action on wood and clay as well as a good stability to alkali on limed substrates.

The active compound according to the invention is also suitable for combating insects, mites, ticks and the like in the field of livestock husbandry and cattle breeding, it being possible to achieve better results, for example higher milk yields, a higher weight, a more attractive animal coat, a longer life and the like, by combating the pests.

The active compound according to the invention is used in this field in the known manner, such as by external use in the form of, for example, dipping, spraying, pouring on and spotting on, and dusting.

The biological activity of the compound according to the invention may be illustrated with the aid of the following examples.

USE EXAMPLES

The compounds shown below are employed as comparison compounds in the use examples which follow:

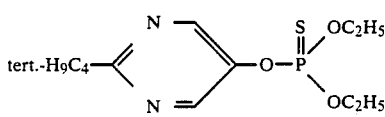

(from U.S. Pat. No. 4,429,125)

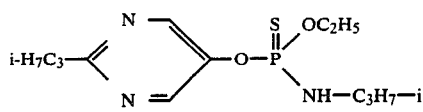

(from DE-OS (German Published Specification) No. 2,643,262)

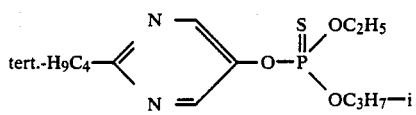

(from DE-OS (German Published Specification) No. 3,317,824)

Example A

Critical concentration test/soil insects
Test insect: Phorbia antiqua maggots (in the soil)
Solvent: 3 parts by weight of acetone
Emulsifier: 1 part by weight alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practially no importance, only the amount by weight of active compound per unit volume of soil, which is given in ppm (=mg/l) being decisive. The soil is filled into pots and these are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% is just as many test insects are still alive as in the case of the untreated control.

In this text, for example, the compound of Example (1) shows a destruction of 100% at a concentration of, for example, 1.25 ppm, while comparison compound (B) resulted in 0% destruction at the same concentration.

Example B

Critical concentration test/root-systemic action
Test insect: Myzus persicae
Solvent: 3 parts by weight of acetone
Emulsifier: 1 part by weight of alkylaryl glycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is filled into pots and these are planted with cabbage (Brassica oleracea). The active compound can in this way be taken up from the soil by the roots of the plants and be transported into the leaves.

To demonstrate the root-systemic effect, exclusively the leaves are infested with the abovementioned test insects after 7 days. After a further 2 days, the evaluation is made by counting or estimating the dead insects. The root systemic action of the active compound is deduced from the mortality figures. It is 100% if all the test insects have been killed and 0% if just as many test insects are still alive as in the case of the untreated control.

In this test, for example, the compound from Example (1) showed a destruction of 100% at a concentration of, for example, 10 ppm, while comparison compounds (A) and (B) resulted in 0% destruction at the same concentration.

Example C

Critical concentration test/nematodes
Test nematode: Meloidogyne incognita
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance, only the amount of active compound per unit volume of soil, which is given in ppm, being decisive. The treated soil is filled into pots, lettuce is sown in and the pots are kept at a greenhouse temperature of 27° C.

After four weeks, the lettuce roots are examined for infestation with nematodes (root galls) and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, the compound of Example (1) showed a destruction of 100% at a concentration of, for example, 10 ppm, while comparison compound (C) resulted in 0% destruction at the same concentration.

Example D $LT_{100}$ test for Diptera
Test animals: Musca domestica (resistant)
Solvent: Acetone 2 parts by weight of active compound are taken up in 1,000 parts by volume of solvent. The solution thus obtained is diluted with further solvent to the desired lower concentration.

2.5 ml of the active compound solution are pipetted into a Petri dish. A filterpaper disc of 9.5 cm diameter is located on the bottom of the Petri dish. The Petri dish is left standing open until the solvent has completely evaporated. The amount of active compound per m² of filterpaper varies, depending on the concentration of the active compound solution. About 25 test insects are then introduced into the Petri dish, and the dish is covered with a glass lid.

The condition of the test insects is checked continuously. The time required for a 100% knock-down effect is determined.

In this test, for example, the compound of preparation Example (1) showed a 100% action after 40, at an active compound concentration of, for example, 0.02%, while comparison compounds (A) and (B) showed a 90 and 100% action only after 6 hours, at the same concentration.

Example E

Test with *Lucilia cuprina* resistant larvae
Emulsifier:
  35 parts by weight of ethylene glycol monomethyl ether
  35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* res. larvae are introduced into a test tube which contains approx. 1 cm³ of horse meat and 0.5 ml of the preparation of active compound. After 24 hours, the degree of destruction is determined.

In this test, for example, the compound of preparation Example (1) showed a destruction of 100% at an active compound concentration of 100 ppm.

Preparation Example 1

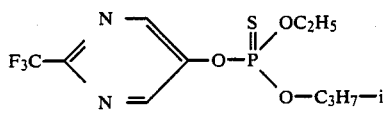

A mixture of 5 g (0.03 mole) of 5-hydroxy-2-trifluoromethylpyrimidine, 6.9 g (0.05 mole) of potassium carbonate, 50 ml of acetonitrile and 6.1 g (0.03 mole) of thiophosphoric acid O-ethyl O-iso-propyl diester-chloride is stirred at 20° C. for 2 hours. After addition of 150 ml of toluene, the mixture is extracted 3 times by shaking with 100 ml of water each time. The organic phase is then dried over sodium sulphate and the solvent is distilled off in vacuo. The residue is subjected to incipient distillation in vacuo at 80° C.

8.8 g (89% of theory) of O-ethyl O-i-propyl O-(2-trifluoromethyl-pyrimidin-5-yl)-thionophosphoric acid ester are thus obtained as a yellow oil with a refractive index $n^{22}$ of 1.4598.

Starting substance of the formula (II)

Example (II-1)

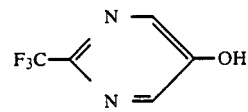

20.5 g (0.123 mole) of 5-fluoro-2-trifluoromethyl-pyrimidine are added to a mixture of 100 ml of ethylene glycol dimethyl ether, 40 ml of water and 25 g of 45% strength sodium hydroxide solution and the mixture is heated under reflux for 2 hours. The solvent is then distilled off in vacuo, 100 ml of water are added to the residue and the undissolved material is filtered off. The filtrate is brought to pH 3.5–4 by addition of concentrated hydrochloric acid at 5°–10° C., while cooling. The product which has precipitated out is filtered off with suction and rinsed with a little cold water.

15.9 g (79% of theory) of 5-hydroxy-2-trifluoromethyl-pyrimidine are thus obtained in the form of colorless crystals of melting point 179°–181° C.

It is understood that the specification and examples are illustrative but not limitatative of the present invention and that other embodiments within the spirit and scope of the invention will suggest themselves to those skilled in the the art.

We claim:
1. O-Ethyl O-isopropyl O-(2-trifluoromethyl-pyrimidin-5-yl)-phosphoric acid ester of the formula

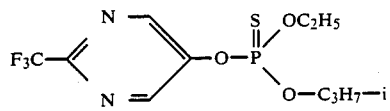

2. An insecticidal or nematocidal composition comprising an insecticidally or nematocidally effective amount of the compound according to claim 1 and a diluent.

3. A method of combating insects or nematodes which comprises applying thereto or to an insect or nematode habitat an insecticidally or nematocidally effective amount of the compound according to claim 1.

* * * * *

UNITED STATES PATENT AND TRADEMARK OFFICE
CERTIFICATE OF CORRECTION

PATENT NO. : 4,774,233

DATED : September 27, 1988

INVENTOR(S) : Fritz Maurer, et al

It is certified that error appears in the above-identified patent and that said Letters Patent is hereby corrected as shown below:

| | |
|---|---|
| Col. 1, line 12 | After "diethyl-0-" delete "0" |
| Col. 2, line 4 | After "hydroxy-2-" delete "thionophosphonic" and substitute --thionophosphoric-- |
| Col. 7, line 60 | After "alkylaryl" delete "glycol" and substitute --polyglycol-- |
| Col. 10, line 29 | Delete "limitatative" and substitute --limitative-- |

Signed and Sealed this

Thirteenth Day of June, 1989

Attest:

DONALD J. QUIGG

Attesting Officer

Commissioner of Patents and Trademarks